(12) United States Patent
Neuberger

(10) Patent No.: US 6,984,229 B2
(45) Date of Patent: Jan. 10, 2006

(54) DEVICE AND METHOD FOR MINIMIZING RESTENOSIS AFTER ANGIOPLASTY TREATMENT

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 46 days.

(21) Appl. No.: 10/103,234

(22) Filed: Mar. 21, 2002

(65) Prior Publication Data
US 2003/0181894 A1 Sep. 25, 2003

(51) Int. Cl.
*A61B 18/18* (2006.01)
(52) U.S. Cl. .............................. 606/15; 606/7; 607/88; 607/89; 604/915
(58) Field of Classification Search ................. 606/7, 606/10, 13–16; 607/88, 89; 604/915
See application file for complete search history.

(56) References Cited

U.S. PATENT DOCUMENTS

| | | | |
|---|---|---|---|
| 4,512,762 A | | 4/1985 | Spears |
| 4,913,142 A | * | 4/1990 | Kittrell et al. ............. 606/7 |
| 5,140,987 A | * | 8/1992 | Schuger et al. ............ 128/642 |
| 5,169,395 A | * | 12/1992 | Narciso, Jr. ................ 606/7 |
| 5,196,005 A | | 3/1993 | Doiron et al. |
| 5,231,684 A | | 7/1993 | Narciso, Jr. et al. |
| 5,607,419 A | * | 3/1997 | Amplatz et al. ............ 606/7 |
| 5,620,438 A | * | 4/1997 | Amplatz et al. ............ 606/10 |
| 5,700,243 A | * | 12/1997 | Narciso, Jr. ............ 604/102.01 |
| 5,776,174 A | * | 7/1998 | Van Tassel ................ 607/89 |
| 5,833,682 A | * | 11/1998 | Amplatz et al. ............ 606/15 |
| 5,957,917 A | * | 9/1999 | Doiron et al. ............ 606/15 |
| 6,004,261 A | * | 12/1999 | Sinofsky et al. ............ 600/36 |
| 6,132,423 A | * | 10/2000 | Aita et al. ................ 606/7 |
| 6,532,387 B1 | * | 3/2003 | Marchitto et al. .......... 604/21 |

* cited by examiner

*Primary Examiner*—A. Farah
(74) *Attorney, Agent, or Firm*—BJ Associates; Bolesh J. Skutnik

(57) ABSTRACT

A novel device and method for preventing restenosis and streamlining the angioplasty procedure. The device and method provide a fiberoptic guidewire, or, alternatively, a light-conducting catheter, to decrease the size of the angioplasty device, decrease the overall time of the procedure, and increase the safety of the procedure. The present invention delivers radiation to a sclerotized area after balloon angioplasty treatment to prevent restenosis Radiation delivered via the catheter or fiberoptic guidewire discourages the cell proliferation and cell growth after angioplasty, thereby improving the chances of avoiding restenosis.

3 Claims, 3 Drawing Sheets

DEVICE AND METHOD FOR MINIMIZING RESTENOSIS AFTER ANGIOPLASTY TREATMENT

BACKGROUND OF THE INVENTION

1. Field of the Invention

This invention relates generally to a method and device using a targeted light source and a photosensitizer to streamline the process of repairing internal body passageways, prevent restenosis, and minimize re-injury after angioplasty treatment.

2. Invention Disclosure Statement

The most common problem with any angioplasty procedure is restenosis, a re-closing of the affected passageway opened by the procedure. This effect is believed to be due to cell proliferation, triggered by the exerted pressure and the lesion caused by the balloon angioplasty. Restenosis occurs in about 30% of patients. The use of stents, or tiny expanding metal scaffolds, is the most common method used to prevent restenosis. However, restenosis through the stent or around the stented area is quite common.

Constrictions in the coronary artery are caused by a buildup of plaque. Plaque can occur in many forms, from a thick viscous consistency (similar to toothpaste) to a rock-hard consistency depending on the proportion of components, which may include calcium, fibrous tissue, fatty deposits, organized clots and thrombus.

Atherosclerosis is a common problem among humans. Fatty substances (lipids), or plaques, form deposits in and beneath the intima—the innermost membrane lining arteries and veins. Atherosclerosis commonly affects large and medium sized arteries. Most commonly affected are the aorta, and the iliac, femoral, coronary, and cerebral arteries. Health problems result from atherosclerosis when reduced blood flow due to constriction of one of the passageways restricts blood flow to a particular tissue or organ. Restricted blood flow compromises and restricts organ or tissue function.

Approximately four million people in the United States suffer from artherosclerotic coronary artery disease. Many of these people are likely to suffer or die from myocardial infarction, commonly known as heart attack. Heart disease is, in fact, the leading cause of death in the United States. Thrombosis in the coronary artery beyond the artherosclerotic constriction is the usual cause of heart attacks. A procedure that can open artherosclerotic constrictions thereby permitting the normal flow of blood to the heart can reduce many deaths and disabilities caused by heart disease.

Modern treatment of atherosclerotic blood passageways usually involves one of two treatments: bypass and/or angioplasty. In bypass treatment, a portion of a blood passageway is borrowed from another area in the body and grafted around the affected passageway. This treatment involves invasive surgery, especially when dealing with the aorta, coronary artery, or other vessels involving the heart. Furthermore, bypass surgery does not heal the affected site, and occurrences of atherosclerosis in the grafted passage are relatively common.

Another method of treating atherosclerosis is angioplasty. In angioplasty, a catheter of some sort is introduced into the passageway. In most methods, the angioplasty catheter, usually equipped with a guidewire, moves along the body passageway to the sclerotized area. A balloon contained inside of the catheter inflates, displacing the plaque and re-opening the passageway.

In another use of the prior art, a photosensitizer is introduced at the sclerotized area prior to introduction of the catheter. After time for the photosensitizer to target and saturate the sclerotized area, a catheter is introduced into the body passageway. Fibers are then inserted into the catheter. The fibers conduct light from some kind of source, i.e. a laser. The laser or other light source activates the photosensitizer in the sclerotized area in order to destroy the plaque. A balloon may or may not be used in this approach to further treat the sclerotized area of the blood passageway. This form of angioplasty is called Photodynamic Therapy (PDT), or intracoronary brachytherapy.

The photoactivating device employed for intracoronary brachytherapy usually comprises a monochromatic light source such as a laser, the light output of which may be coupled to an invasive light delivery catheter for conduction and delivery to a remote target tissue. Such interventional light delivery catheters are well known in the art and are described, for example, in U.S. Pat. No. 4,512,762 (Spears). In that invention a balloon is illuminated to activate the photosensitizer.

Generally, the prior art of intracoronary brachytherapy involves at least five steps: insertion of a guidewire; insertion of a catheter over the guidewire; removal of the guidewire; insertion of a fiberoptic wire; and finally, irradiation. The present invention is a method to prevent restenosis by using a novel catheter with light conducting means and a targeting mechanism for focusing that light source on a photosensitizer to treat a sclerotized area of a human body passageway. Most balloon angioplasty procedures do not involve radiation to prevent cell growth in the intima. Instead, they aim to compress or displace cells in a sclerotized vessel with a stent or other means. These treatments tend to encourage restenosis by stimulating a responsive force in the vessel wall, or stimulating the proliferation of cells in the area to re-take its original shape.

The present invention provides a non-mechanical method and product for preventing restenosis by irradiation. A "fiberoptic guidewire" assists the doctor or technician in navigating body passageways, and also conducts radiation to its own diffuser to engage in PDT. Alternatively, a balloon catheter is manufactured to conduct radiation to an obstructed body passageway. Either embodiment streamlines the angioplasty procedure.

OBJECTIVES AND BRIEF SUMMARY OF THE INVENTION

It is an object of the present invention to provide a method to prevent or minimize occurrences of restenosis after angioplasty.

It is also an object of the present invention to streamline the process of angioplasty to reduce patient exposure and increase the safety of the process.

It is another object of the present invention to provide a guidewire capable of transmitting radiation, hereinafter referred to as a "fiberoptic guidewire," to streamline the angioplasty process and prevent restenosis.

It is a further object of the present invention to provide a fiberoptic guidewire with a diffuser end capable of transmitting radiation to a sclerotized body passageway.

It is still another object of the present invention to provide a catheter manufactured to conduct radiation, either by insertion of optical fibers in the tubular structure or by manufacturing the catheter of a homogeneous light-conducting polymer.

Briefly stated, the present invention provides a novel device and method for preventing restenosis and streamlining the angioplasty procedure. The device and method provide a fiberoptic guidewire, or, alternatively, a light-conducting catheter, to decrease the size of the angioplasty device, decrease the overall time of the process, and increase the safety of the procedure. The present invention delivers radiation to a sclerotized area after balloon angioplasty treatment to prevent restenosis. Radiation delivered via the catheter or fiberoptic guidewire discourages the cell proliferation and cell growth after angioplasty, thereby improving the chances of avoiding restenosis.

The above, and other objects, features and advantages of the present invention will become apparent from the following description read in conjunction with the accompanying drawings.

DETAILED DESCRIPTION OF PREFERRED EMBODIMENTS

The entire angioplasty process is streamlined considerably by the present invention. In the present state of the art, there are several steps to the angioplasty procedure: Introduction of a standard guidewire; introduction of a catheter over a guidewire; removal of the guidewire; introduction of an optical fiber; inflation of the balloon, irradiation, and removal of the entire system. In the present invention, light radiation is transmitted through the fiberoptic guidewire, or alternatively the catheter. The length and complication of the angioplasty process is greatly decreased. A fiberoptic guidewire eliminates the need for of different means for navigation and irradiation. The prior art provides for separate fibers or possibly separate lumens in the catheter for movement over the guidewire and transmission of radiation. The present invention streamlines the process by combining the functions of the guidewire and radiation transmitter, or by transmitting radiation via the catheter itself. The manufacture of a catheter with light-conducting properties also alleviates the need for removal of the guidewire and insertion of a means of irradiation. Decreasing the amount of time that a vessel is subject to a foreign body increases the safety of the process. In addition, the size of the device decreases with the decreased need for lumens for a guidewire, gas, and fiberoptic transmission.

Figure 1:
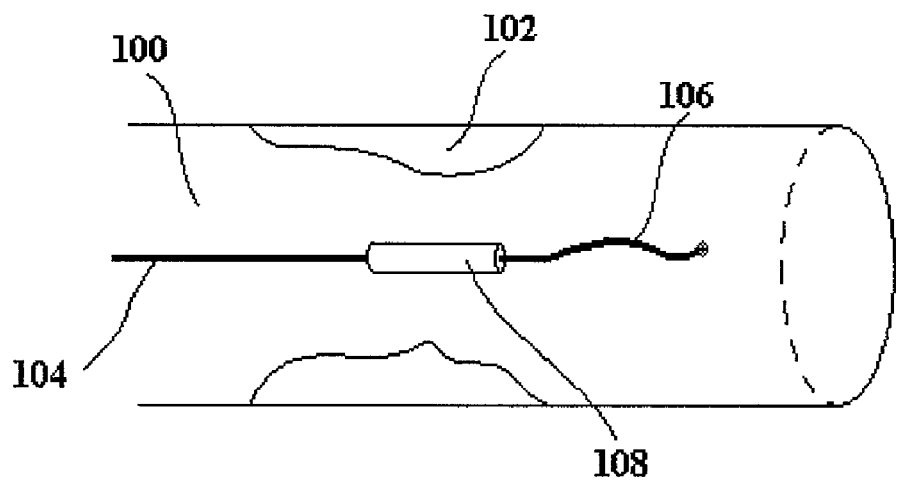
FIG. 1 shows a fiberoptic guidewire with a diffuser in a sclerotized body passageway.

In one preferred embodiment, a fiberoptic guidewire is manufactured in accordance with FIG. 1. This fiberoptic guidewire alleviates the need for a separate fiber or wire for irradiation.

A photosensitizer is introduced at a sufficient time prior to beginning the minimally invasive procedure to allow for, preferably, location and targeting of the sclerosis and/or plaque. The fiberoptic guidewire is then introduced into the body passageway. The fiberoptic guidewire has a diffuser located near the distal end. The diffuser will allow for homogeneous and/or differential distribution of radiation at a selected power and intensity to discourage growth and proliferation of the cells in either the vessel walls or the plaque. Various methods of creating homogeneous diffusion are known in the prior art. U.S. Pat. No. 5,196,005 (Doiron & Narcise) describes a method for placing diffusion tips on optical fibers. U.S. Pat. No. 5,231,684 (same inventors) describes the use of a microlens attached to the end of an optical fiber for diffusion of radiation. The present invention envisions a diffuser with a section of guidewire extending distally for optimal navigation in a body passageway. A variation of the prior art that allows an extension of guidewire distally from the distal end of the diffuser is used in the present invention.

Extending distally from the diffuser, a short piece of guidewire allows for conventional navigational advantages of a guidewire for location of the affected area of the body passageway. The proximal end of the fiberoptic guidewire extends from the diffuser through the body passageway to the portion exiting from the patient and connected to the light source. Methods and devices to allow handling and movement of the guidewire by a doctor or technician are known in the prior art.

Figure 2:
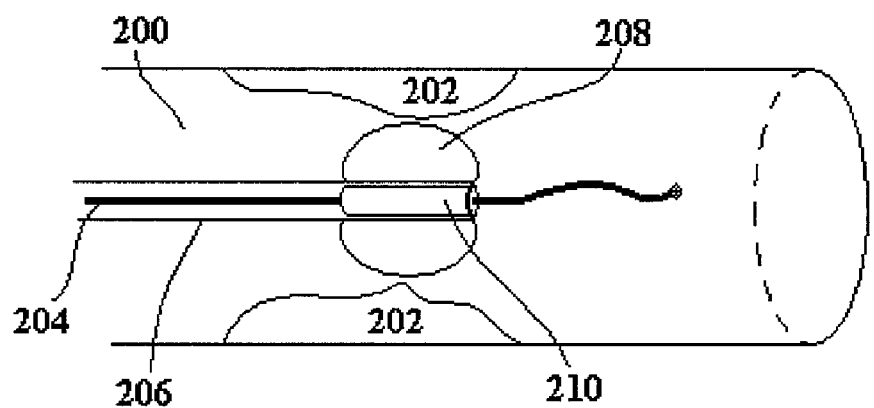
FIG. 2 is a continuation of FIG. 1, showing a balloon catheter circumscribing the fiberoptic guidewire in the sclerotized body passageway.

By using the described fiberoptic guidewire, the means to transmit radiation are in place. A balloon catheter is then introduced that circumscribes the guidewire, as shown in FIG. 2. After proper positioning of the catheter, the balloon is inflated to displace the plaque. The light source connected to the proximal end of the guidewire is then activated, irradiating the plaque and vessel walls. Irradiating the plaque and activating the photosensitizer located within the plaque discourages cell proliferation and growth—two responses by the cell wall and/or plaque buildup to an exerted force (the angioplasty balloon) that cause restenosis in 30% of patients that receive angioplasty treatment.

In another preferred embodiment, the light conducting means are located within the catheter. In this device, a photosensitizer is again introduced. A standard, non-fiberoptic guidewire is introduced to assist the doctor or technician in navigating the body passageway to the sclerosis or constriction. The balloon catheter, again circumscribing the guidewire, is introduced and navigated along the guidewire to the affected area.

The catheter is manufactured to conduct radiation to the affected area. In one variation of the present embodiment, the tubular structure of the balloon catheter is manufactured in accordance with FIG. 4. Optical fibers embedded in the tubular structure are enclosed in lumens that allow space for differential bending and extension/contraction of the fibers as opposed to the catheter body itself. Fibers of quartz, glass, and plastic are known in the field of fiberoptics and are suitable for use in this embodiment. At least one other lumen exists for free movement of the guidewire relative to the catheter.

The larger lumens for optical fibers can also be used for transmission of a gas or liquid for inflation of the balloon. The use of gases or liquids for inflation of a balloon catheter is well known in the art. U.S. Pat. No. 4,512,762 (Spears) describes the use of a lumen to transmit pressurized gas to a balloon catheter for inflation. The optical fibers extend distally to the balloon itself, where they transmit radiation to the balloon. Upon inflation of the balloon and displacement of the plaque, the light source is activated, transmitting radiation along the optical fibers and to the inflated balloon.

The means of transmission is designed for homogeneous or, if desired, differential transmission of radiation throughout the balloon to the sclerotized area for maximum irradiation.

The irradiation of the plaque and vessel walls activates the photosensitizer and prevents restenosis by discouraging cell growth and cell proliferation in the vessel walls and the plaque. These processes of growth and proliferation are generally attributed as causes of restenosis.

Figure 5:
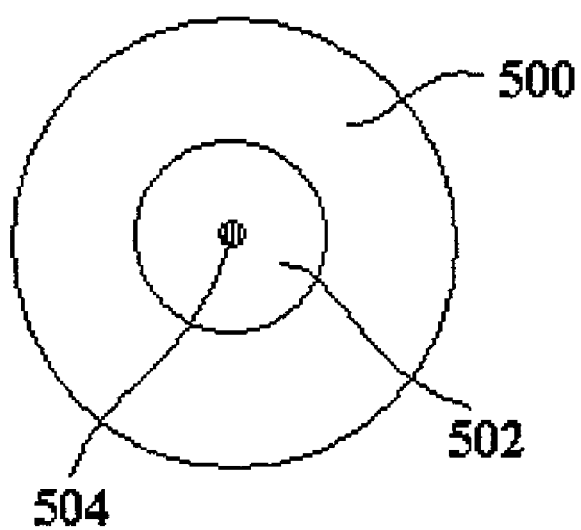
FIG. 5 is another embodiment of the catheter of the present invention, manufactured from a light-conducting polymer.

In another variation of this preferred embodiment, the catheter body itself is manufactured using a homogeneous light-conducting polymer in accordance with FIG. 5. This polymer will conduct radiation from a light source on its proximal end to the affected area through the angioplasty balloon. At the distal end of the catheter, a diffuser section of the catheter transmits radiation from the catheter walls to the balloon or directly to the plaque and vessel wall. There are several diffusers that are well known in the field of PDT that can be used, or variations of those diffusers can be manufactured to ideally suit the present application.

The catheter contains at least one lumen for circumscribing the guidewire and transmission of a liquid or gas for inflation of the catheter balloon. In this variation, the angioplasty procedure would be similar to the previous variation. The photosensitizer is introduced; a guidewire is inserted. The catheter is inserted over the guidewire, and the balloon is inflated, displacing the obstruction in the body passageway. The area is then irradiated, preventing restenosis.

Once again, the angioplasty procedure is streamlined by introduction of a catheter with light-conducting properties designed specifically for transmission of radiation to an obstruction in a human blood vessel or other body passageway eliminates the need for a separate fiber introduced solely for the purpose of transmitting radiation. The time saved in the procedure translates into increased safety for the patient undergoing angioplasty treatment.

The present invention is further illustrated by the following examples, but is not limited thereby.

EXAMPLE 1

FIG. 1 shows body passageway 100 affected with obstruction 102. The distal end 106 of guidewire 104 extends beyond diffuser 108, which is positioned at obstruction 102. The guidewire 104 is constructed of a fiberoptic material, allowing for conduction of radiation during the angioplasty process. As shown in FIG. 2, balloon catheter 206 is inserted into body passageway 200, circumscribing the guidewire 204 up to the end of the diffuser 210. When the catheter 206 is properly positioned, balloon 208 is inflated, displacing plaque or other obstruction 202. After displacement, a light source connected to the proximal end of guidewire 204 is activated, transmitting radiation to diffuser 210 and through balloon 208. The irradiation stops the re-growth and proliferation of plaque or other obstructions that cause restenosis.

EXAMPLE 2

Figure 3:
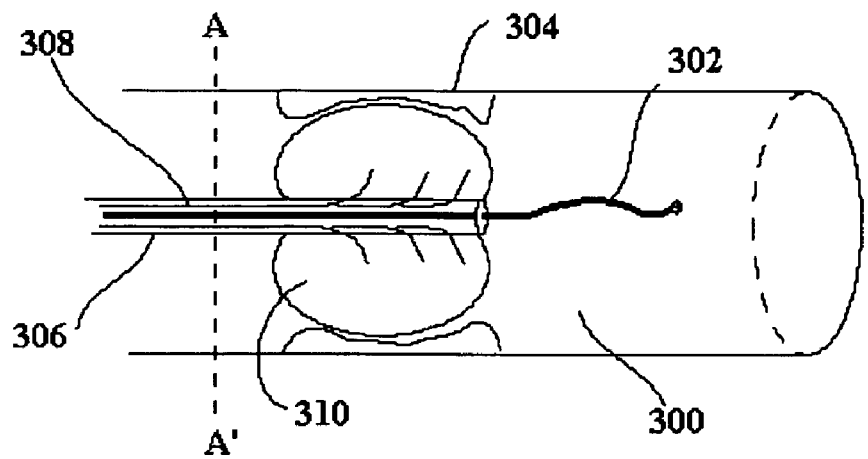
FIG. 3 shows a balloon catheter equipped with optical fibers in its tubular structure circumscribing a conventional guidewire.
Figure 4:
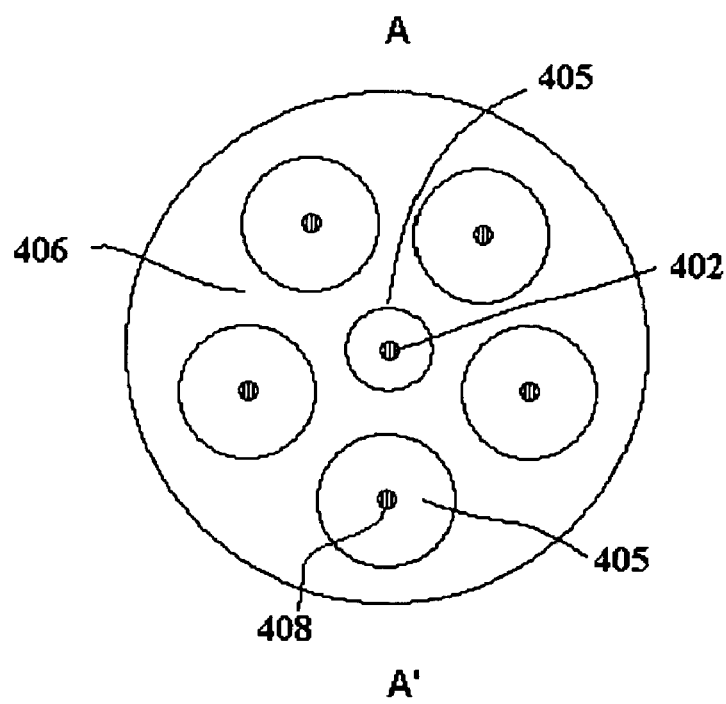
FIG. 4 is a cross section of the catheter described in FIG. 3 down its longitudinal axis.

FIG. 3 shows a conventional guidewire 302 circumscribed by a catheter in an affected body passageway 300. The guidewire 302 is inserted, the distal tip extending a distance beyond the affected area 304. The balloon catheter 306 is then introduced, circumscribing the guidewire 302. Optical fibers 308 are contained within the tubular structure of catheter 306. The angioplasty balloon is positioned at obstruction 304 and inflated. The balloon 310 displaces plaque 304. A light source connected to the proximal end of optical fibers 308 is activated, transmitting radiation to balloon 310. Irradiation of the plaque 304 prevents cell growth and regeneration, the causes of restenosis. FIG. 4 shows a cross section, looking down the longitudinal axis, of catheter 406. Lumens 405 are circular or otherwise shaped for optimal sizing of the catheter wall structure 406. Optical fibers 408 are smaller than lumens 405 to allow for movement and to prevent cracking or breaking of fibers 408. At least one lumen 405 exists in the catheter wall 406 for transmission of a gas or liquid for inflation of the angioplasty balloon. One lumen exists centrally within the catheter for circumscribing the guidewire 402.

EXAMPLE 3

In a variation of Example 2 shown in FIG. 5, catheter body 500 is manufactured as a light-conducting polymer. The catheter 500 contains at least one lumen 502 for transmission of gas or liquid to inflate the catheter and to circumscribe the guidewire 504. The processes of angioplasty and irradiation are similar to Example 2. Radiation is transferred through the light-conducting body of the catheter 500 to an angioplasty balloon in sufficiently homogeneous form to transfer to the angioplasty balloon when inflated, irradiating the obstruction in the body passageway. This homogeneous transmission can be accomplished by use of a simple diffuser. The diffuser transmits radiation from the polymer-based catheter body 500 to the balloon or directly to the obstructed area of the body passageway.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. An improved angioplasty catheter system, which reduces occurrence of restenosis, and reduces the number of operational steps in a treatment, wherein said system comprises:

a balloon catheter having a balloon at a distal end of said catheter, said catheter having a wall at a distal end being transparent to homogeneous radiation;

a guidewire surrounded by said catheter's body/wall;

means for providing said homogeneous radiation to a treatment site after or during dilation of an occluded section;

means for scattering said radiation outward from optical fibers at said distal end of said catheter;

wherein said radiation activates a previously introduced photodynamic therapy composition present at said treatment site; and wherein said means for providing radiation is integrated into said angioplasty catheter system as part of said catheter's wall and is employed without removal of said guidewire used to place said catheter at said treatment site, wherein said catheter's wall has channels in which are optical fibers, wherein said optical fibers within said channels are means for providing said homogeneous radiation; wherein at least one of said channels also function to inflate said balloon of said angioplasty catheter system.

2. A streamlined method of angioplasty, using the improved angioplasty catheter system of claim 1, to reduce occurrence of restenosis comprising the steps of:

a) introducing a photosensitizing moiety or its precursor into a patient and allowing it to enter said patient's blood vessels;
b) introducing a guidewire into a patient at a preselected time after step a) and advancing said guidewire to an occluded section within said patient's blood vessel;
c) slipping a balloon catheter according to claim 1 over said guidewire and positioning a balloon within a preselected occluded section of said patient's blood vessels;
d) dilating said occluded section of said patient's blood vessel at a preselected treatment site; and
e) homogeneously irradiating said dilated section at said treatment site to activate said photosensitizing moiety using means integrated with said balloon catheter as provided by said catheter system according to claim 1, wherein said balloon catheter is selected from the group consisting of optical fibers in channels within said catheter's wall, and a light-transmitting catheter wall which transmits said radiation.

3. An improved angioplasty catheter system, which reduces occurrence of restenosis, and reduces the number of operational steps in a treatment, wherein said system comprises:

a balloon catheter having a balloon at a distal end of said catheter, said catheter having a light transmitting catheter wall and a proximal end and a distal end, wherein said catheter wall transmits a radiation from a source on said proximal end to said distal end, a section of said catheter wall at said distal end having means for scattering outward said radiation in said catheter wall at said distal end of said catheter wherein said catheter's wall has channels in which are optical fibers, wherein said optical fibers within said channels are means for providing said homogeneous radiation; wherein at least one of said channels also function to inflate said balloon;

a guidewire surrounded by said catheter's body/wall;

means for providing homogeneous radiation to a treatment site after or during dilation of an occluded section;

wherein said radiation activates a previously introduced photodynamic therapy composition present at said treatment site; and wherein said means for providing radiation is integrated into said angioplasty catheter system as part of said catheter's wall and is employed without removal of said guidewire used to place said catheter at said treatment site.

* * * * *